United States Patent [19]

Schwabe et al.

US005753711A

[11] Patent Number: 5,753,711
[45] Date of Patent: May 19, 1998

[54] **METHOD FOR TREATMENT OF *H. PYLORI***

[75] Inventors: Christian Schwabe, Charleston, S.C.; Robert A. Ashley, Newtown, Pa.

[73] Assignee: Collagenex Pharmaceuticals, Inc., Newtown, Pa.

[21] Appl. No.: 819,734

[22] Filed: Mar. 18, 1997

[51] Int. Cl.$^6$ .................................................. A61K 31/14
[52] U.S. Cl. ............................................................ 514/643
[58] Field of Search ................................................ 514/643

[56] References Cited

U.S. PATENT DOCUMENTS

| | | |
|---|---|---|
| 4,748,113 | 5/1988 | Marshall . |
| 4,994,262 | 2/1991 | Charbonneau et al. ............ 424/52 |
| 5,145,664 | 9/1992 | Thompson ............................ 424/49 |
| 5,447,923 | 9/1995 | Catrenich et al. . |
| 5,472,695 | 12/1995 | Neeman et al. . |
| 5,504,082 | 4/1996 | Kawakita et al. . |
| 5,549,901 | 8/1996 | Wright . |
| 5,560,912 | 10/1996 | Neeman et al. . |

FOREIGN PATENT DOCUMENTS

| | | |
|---|---|---|
| 08020543 | 1/1996 | Japan . |
| WO 96/02236 | 2/1996 | WIPO . |
| 96/24341 | 8/1996 | WIPO . |

OTHER PUBLICATIONS

*Helicobacter pylori* and Gastrointestinal Disease, J. Clin. Pharmacol. 35:647–654 (1995).

Detection of *Helicobater pylori* in Dental Plaque by Reverse Transcription–Polymerase Chain Reaction, J. Clin. Microbial 31:783–787 (1993).

*Helicobacter pylori* in the Oral Cavity, A Critical Review of the Literature, Oral Surg. Oral Med. Oral Pathol. Oral Radial. Endod. 76:705–9 (1995).

High Prevalence of *Helicobacter pylori* in Saliva Demonstrated by a Novel PCR Assay, J. Clin. Pathol. 48:662–666 (1995).

Transmission of *Helicobacter pylori* : Faecol–Oral Versus Oral–Route, Alimentary Pharmacology & Therapeutics, 9 Suppl. 2:85–91 (1995).

*Helicobacter pylori* and Peptic Ulcer Disease, American Journal of Roentgen 164:283–286 (1995).

*Helicobacter pylori* and Peptic Ulcer Disease, New England Journal of Medicine 324:1043–1048 (1991).

Lose Dose, Short–Term Triple Therapy for Cure of *Helicobacter pylori* Infection and Healing of Peptic Ulcers, American Journal of Gastroenterology 6:943–945 (1995).

The Treatment of *Helicobacter pylori* Infection in the Management of Peptic Ulcer Disease, New England Journal of Medicine 333:984–991 (1995).

Toward an Optimal Treatment of *Helicobacter pylori*—Positive Peptic Ulcers, American Journal of Gastroenterology 90:692–694 (1994).

Reynolds, et al. "Martindale The Extra Pharmacopoeia". 28th ed. (The Pharmaceutical Press, London), pp. 549–550, 1982.

Lee, Scand. J. Gastroenterol. Suppl. (Norway), 29/201 (2–6), Embase abtract No. 94154861, 1994.

Li, et al. J. Clin. Pathol. (England), 48(7) pp. 662–666 (Medline Abstract), Jul. 1995.

Lambert et al., Scand. J. Gastroenterol. Suppl. (Norway), 208, pp. 33–46 (Medline Abstract), 1995.

Takeshi, Prog. Med. vol. 16, No. 6, pp. 1543–1545 (Japan Science and Tach Corp. Abstract), 1996.

Akamatsu, et al., American Journal of Infection Control 24(5), pp. 396–401 (Biosis Abstract), 1996.

*Primary Examiner*—Raymond Henley, III
*Attorney, Agent, or Firm*—Hoffmann & Baron, LLP

[57] ABSTRACT

In a method for preventing the spread of *Helicobacter pylori* from the oral cavity, the oral cavity is contacted with alkyldimethylammonium chloride. The contacting is advantageously used in conjunction with enteric antimicrobial therapy for *H. pylori* or for prophylaxis thereof.

11 Claims, No Drawings

METHOD FOR TREATMENT OF *H. PYLORI*

This invention relates to a method for preventing the oral transmission of *Helicobacter pylori* by contacting the oral cavity with alkyldimethylammonium chloride.

BACKGROUND OF THE INVENTION

*Helicobacter pylori* is found in the gastrointestinal tract and is implicated in gastritis, peptic ulcer disease and gastric cancer. See, e.g. a review by M. Gibaldi, "*Helicobacter pylori* and Gastrointestinal Disease", J. Clin. Pharmacol., 35,647–654 (1995). *H. pylori* was previously called *Campylobacter pylori* or *Campylobacter pyloridis*.

The presence of *Helicobacter pylori* is also reported in saliva and dental plaque. In an investigation of whether the oral cavity is a reservoir for *H. pylori*, gastric biopsy and dental plaque from dyspeptic patients show both sites infected with the same strain of a *Helicobacter pylori*. A-M H. Nguyen, et al., "Detection of *Helicobacter pylori* in Dental Plaque by Reverse Transcription - Polymerase Chain Reaction", J. Clin. Microbiol., 31(4), 783–7 (1993). Failure to eliminate *H. pylori* from the mouth in antimicrobial therapy can lead to recolonization of the stomach. A-M H. Nguyen, et al., "*Helicobacter pylori* in the Oral Cavity", Oral Surg. Oral Med. Oral Path. Oral Radiol. Endod. 76, 705–9 (1995).

C. Li, et al., "High Prevalence of *Helicobacter pylori* in Saliva Demonstrated by a Novel PCR Assay", J. Clin. Pathol., 48(7), 662–6 (1995) also confirm that the oral cavity harbors *Helicobacter pylori* and may be the source of infection and transmission.

It is suggested that person-to-person transmission of *H.pylori* can be fecal-oral or oral-oral. F. Megraud, "Transmission of *Helicobacter pylori*: Faecal-Oral versus Oral-Oral Route", Alimentary Pharmacology & Therapeutics, 9 Suppl. 2, 85–91 (1995). One transmission mode is likely person-to-person by oropharyngeal secretions. J. P. Cello, "*Helicobacter pylori* and Peptic Ulcer Disease", AJR, 164, 283–286 (1995).

*Helicobacter pylori* enteric infections have proven to be difficult to treat. W. L. Petersen, "*Helicobacter pylori* and Peptic Ulcer Disease", N. Engl. J. Med., 324 (15), 1043–1048 (1991). See also, U.S. Pat. Nos. 5,447,923, 5,472,695, 5,504,082 and 5,560,912. Often a triple therapy containing bismuth compound and two antibiotics is recommended. B. H. Jaup and A. Norrby, "Low Dose, Short-Term Triple Therapy for Cure of *Helicobacter pylori* Infection of Healing of Peptic Ulcers", AJG 90,943–945 (1995). See also, International Application WO 96/02236.

However, there is a dirth of information on how to eradicate *H. pylori* in the mouth.

JP 8-20543 describes oral application, e.g., as a mouthwash, of a bismuth compound for a bacteriocidal effect against *Helicobacter pylori* in preventing and treating gastrointestinal disorders and their recurrence. Unfortunately, Bismuth compounds such as bismuth subsalicylate (e.g., Pepto-Bismol®) in high doses have a side effect of central nervous system toxicity. See, e.g., J. H. Walsh and W. L. Peterson, "The Treatment of *Helicobacter pylori* Infection in the Management of Peptic Ulcer Disease", N. Engl. J. Med., 333(15), 984–991 (1995), p. 987.

In addition, bismuth compounds alone, when administered enterically, are found to be inadequate for bacteriolysis of *H. pylori* so that the use of bismuth requires co-administration of antibiotics. J. Labenz and G. Borsch, "Toward an Optimal Treatment of *Helicobacter Pylori*-Positive Peptic Ulcers", AJG, 90(5), 692–694 (1995).

It is generally agreed that substantially complete eradication of *H. pylori* in infected subjects is necessary to prevent recurrent disease. See, e.g., a review by J. H. Walsh, and W. L. Peterson, "The Treatment of *Helicobacter pylori* Infection in the Management of Peptic Ulcer Disease", N. Engl. J. Med., 333(15), 984–91 (1995).

The persistence of *H. pylori* in the mouth presents a reservoir of organisms for potential reinfection and transmission. This problem has not yet been adequately addressed.

There is still a need for a method of eradicating *H. pylori* in the mouth so that gastro-intestinal infection or reinfection from the oral reservoir, or person-to-person transmission from the oral reservoir can be avoided.

SUMMARY OF THE INVENTION

The present invention provides a method for preventing the spread of *Helicobacter pylori* from the oral cavity. The organism can spread from the oral cavity to the gastrointestinal tract of a subject; or can be transmitted from person-to-person through oral contact, possibly through saliva contamination.

The spread of *Helicobacter pylori* can be prevented by treating or contacting the oral cavity with a composition comprising alkyldimethylammonium chloride. The composition is used in an effective antibacterial amount to exert a bacteriocidal and/or bacteriostatic effect.

The treating or contacting can be accomplished by with a composition containing alkyldimethylammonium chloride in a preferred amount of about 0.10% by weight to 2.5% by weight, more preferably from about 0.12% to about 0.20% or 0.25% by weight. The contacting can be accomplished using a mouthwash, toothpaste or aerosol spray, all of which contain alkyldimethylammonium chloride. When the composition is used in the form of a toothpaste, the toothpaste preferably contains a higher level, e.g. up to 2.5% by weight, of the alkyldimethylammonium chloride and no detergents.

Preferably the treatment is carried out concurrently with or following administration of known antimicrobial methods of treating *H. pylori* infections in the gastro-intestinal tract. Prophylactic treatment of the oral cavity is also advantageous.

The treatment results in the interruption of occurrence or recurrence of gastritis or peptic ulcers caused by *Helicobacter pylori* and the prevention of person-to-person transmission of *Helicobacter pylori*.

When the method is used in conjunction with enteric antimicrobial therapy, a more thorough eradication of the organism is accomplished.

DETAILED DESCRIPTION OF THE INVENTION

*H. pylori* is a fastidious, microaerophilic, gram negative bacterium which is a spirally curved rod having mobility with one or more flagella. The organism resides in mucus layer of the gastric mucosa and in the oral cavity.

The method of the invention effectively eliminates *H. pylori* in the mouth by oral application of alkyldimethylammonium chloride (BAC). A preferred composition consists essentially of BAC solution as the active ingredient for anti-*H. pylori* effect. The BAC solution is effective by itself, but sodium chloride made be added to amplify the adherence of the BAC to gingival and tooth surfaces. The dissociation of the BAC from the surface is advantageously very slow as demonstrated by the persistence of a slight bitterness and the lack of mal odor. The bitter taste can be removed by tooth-brushing. While the BAC persists, it continues to exert an anti-*H. pylori* effect.

BAC suitable for use in the invention is a mixture of alkyldimethylbenzylammonium chlorides of the general formula

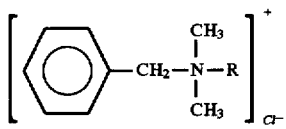

in which R represents a mixture of alkyls from $C_8H_{17}$ to $C_{18}H_{37}$. *The Merck Index*, S. Budavari, ed., Merck & Co., Inc., Eleventh Edition 1989, entry 1066.

In the invention, the BAC used is an equimolar mixture of alkyldimethylbenzylammonium chlorides having a straight chain alkyl substituent of from 12 to 18 carbons. The BAC can be called benzalkonium chloride. BAC is commercially available as a compound for use in cold sterilization of surgical instruments. Some of these commercially available BAC's are Benirol, Capitol, Cequartyl, Drapolene, Germinol and Zephiran Chloride.

The BAC solution is preferably prepared in water. Alcohols may also be added, usually as carriers for taste and color additives. An example of a suitable alcohol is ethanol in an amount of about 1%–2%.

The BAC can be employed in admixture with conventional excipients suitable for oral application and which do not deleteriously react with the BAC. Suitable pharmaceutically acceptable carriers include, but are not limited to, water, salt solutions, gum arabic, vegetable oils, perfume oils such as peppermint, fatty acid monoglycerides and diglycerides, pentaerythritol fatty acid esters, polyvinylpyrrolidone, glycerin, etc; also, auxiliary agents, e.g., diluents, lubricants, stablilizers, wetting agents, emulsifiers, salts for influencing osmotic pressure, buffers, flavoring agents, etc.

Additional inactive components may be added to adjust viscosity, taste, appearance or other physical properties. Viscosity enhancing substances include, e.,g., glycerin and cellulose compounds. Amounts for these components can be determined by routine experimentation to achieve the desired effect. However, a low viscosity is perferred for mouthwash applications since BAC in a fluid medium transfers faster to oral tissues, such as gingiva.

The BAC is dissolved in water to form a mouthwash, which can be formulated as a gel as well as a liquid. For simplicity, economy and function, a liquid is preferred. The BAC formulation can also be incorporated into a dentifrice or spray.

For the BAC composition used in the invention, a solution of the components is prepared in water or other carrier in amount to result in 100 weight percent total composition. The pH of the composition is preferably compatible with oral tissues. The composition can optionally include additives to enhance the appearance or taste of the composition, for example, alcohol up to about 2 weight percent, and coloring and/or, flavoring agents as are known in the art. Non-limiting examples of flavoring agents include the mint-flavorings such as oil of spearmint, oil of peppermint and oil of wintergreen; and other oils including citrus, clove, eucalyptus, etc. Colorants may be chosen from those approved by the U.S. Food and Drug Administration (FDA), such as Blue Nos. 1 and 2. Green No. 6, Red Nos. 3 and 40, and Yellow Nos. 5 and 6. Non-fermentable sugars or sugar substitutes may also be added where a sweetened vehicle is desired. These include sugar alcohols, sorbitol, xylitol, maltitol, saccharines, aspartame (useful only at neutral pH), sucaryl or the like. Flavorants and sweeteners are used in small amounts, e.g., up to about 0.25 weight percent, preferably up to about 0.05 weight percent.

Known anti-stain additives e.g. in an amount of about 0.01 to 0.1 weight percent, may also be added, such as phosphorous-containing and organo-phosphorous-containing compounds. But for staining which may occur, it is preferred to utilize the composition of the invention both as a mouth rinse and incorporated into a toothpaste, for example as a gel component. In a preferred treatment method which avoids staining, both a mouth rinse and a tooth brushing with the composition of the invention are undertaken in the morning, while in the evening, the mouth rinse alone is used. However, the composition can always be used in mouthwash form alone.

Additives which adversely interact with BAC should be avoided, for example, surfactants, particularly anionic surfactants.

The composition is applied preferably as an oral lavage or rinse. The composition can also be orally administered in an aerosol spray. *H. pylori* infection becomes more prevalent with increasing age, and since older patients and others often have removable dental bridges or appliances, the composition can also be added to denture cleaning formulations for thorough eradication of *H. pylori* which may be deposited from saliva. Soaking in a solution containing about 0.25% BAC is preferably followed by brushing of the bridge or dental appliance.

When a mouthwash is used, oral contact with the mouthwash is maintained for at least from 5 to 15 seconds. The mouthwash may also be advantageously gently introduced into the lumen of a periodontal pocket or periodontal abscess using a blunt-needled syringe.

A toothpaste or dentifrice according to this invention contains BAC and optionally sodium chloride in an otherwise conventional toothpaste formulation containing components which do not interfere with the composition, e.g., a dentifrice preferably containing abrasives such as insoluble organic salts, thickening agents (carrageenan), flavorings, foaming agent, humectant (glycerol, sorbitol), and water. Standard abrasives include dicalcium phosphate, insoluble sodium metaphosphate, calcium pyrophosphate, calcium or magnesium carbonate, hydrated aluminum oxide, silicates and dehydrated silica gels.

For a spray application, the BAC composition, optionally in combination with other carrier material, may be packaged in a squeeze bottle or in admixture with a pressurized volatile, normally gaseous propellant. The oral cavity is preferably rinsed with water within a minute or so after the spray is used.

Appropriate ingredients such as additives which are generally recognized as safe (GRAS) or approved under the Federal Food, Drug and Cosmetic Act (FD & C Act; 21 U.S.C. 321) may be added to the composition of the invention in any of its forms.

Since the method of the invention is not associated with toxicity or side effects, the duration of treatment is limited only by practical considerations. Indeed, routine mouthrinsing according to the invention is a recommended prophylaxis for *H. pylori*.

The following illustrative examples are not intended to limit the invention.

EXAMPLE 1

A solution of 0.17% by weight benzalkonium chloride in water was prepared. Dilutions of 1:10 and 1:100 of this solution were tested for bacteriocidal effect on *Helicobacter pylori* grown on blood agar.

*H. pylori* was first grown on blood agar to colony confluence so that the surface of the plates was completely covered with the bacterial growth.

Twenty microliters of the 1:10 and 1:100 solutions were applied to the surface of confluent plates. After observation times of one hour and 24 hours, the application of the 1:10 dilution resulted in a large circle of killed bacteria. The 1:100 dilution produced a smaller circle.

CLO test is a very sensitive test for the live bacteria. CLO tests taken from both circles were negative for *H. pylori* while test samples from outside the circles were positive for *H. pylori*. A commercially available CLO test is described in U.S. Pat. No. 4,748,113. In the CLO test, a medium containing urea with pH sensitive indicator such as phenol red is inoculated with the sample. *H. pylori* has potent urease activity, which causes urea to be split into $CO_2$ and ammonia resulting in an increase in pH and a change in the color of the indicator.

EXAMPLE 2

The bacteriostatic effect was tested. One half of a blood agar plate was impregnated with a 0.17% solution in water of benzalkonium chloride while the other half remained untreated as a control. Both sides were streaked with a suspension of *H. pylori* and the plate was incubated. On observation at one day and observations three to four days later, the benzalkonium chloride side of the plate was completely free of growth while heavy growth was observed on the control side.

EXAMPLE 3

The general *H. pylori* bacteriocidal effect of the 0.17 % solution of benzalkonium chloride in the oral cavity of a person was tested by streaking saliva on a blood agar plate before a mouth rinse with the solution and after the mouth rinse. The plate streaked with saliva before the mouth rinse was heavily overgrown after twelve hours incubation while the sample taken after the mouthwash was essentially free of growth.

These examples show that oral application of benzalkonium chloride is effective to interrupt the oral route of infection or reinfection with *H. pylori*.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

We claim:

1. A method for preventing the transmission of *Helicobacter pylori* comprises contacting the oral cavity of a subject susceptible to *Helicobacter pylori* with a composition comprising alkyldimethylammonium chloride, said alkyldimethylammonium chloride in an effective antibacterial amount for *Helicobacter pylori*.

2. The method of claim 1 wherein the transmission is from the oral cavity of the subject to the gastrointestinal tract of the subject.

3. The method claim 1 wherein the transmission is from subject to subject.

4. The method of claim 1 wherein the subject is a mammal.

5. The method of claim 1 wherein the subject is human.

6. The method of claim 1 wherein the composition is incorporated into a mouthwash, dentifrice, or aerosol spray.

7. The method of claim 1 wherein the alkyldimethylammonium chloride is in an amount of from about 0.1% to about 2.5% by weight.

8. The method of claim 1 wherein the alkydimethylammonium chloride is benzalkonium chloride.

9. The method of claim 1 wherein the contacting is concurrent with antimicrobial treatment for gastrointestinal *H. pylori*.

10. The method of claim 1 wherein the contacting is after antimicrobial treatment for gastro-intestinal *H. pylori*.

11. The method of claim 1 wherein the treatment is prophylactic for infection with *H. pylori*.

* * * * *